United States Patent
Choate et al.

(10) Patent No.: US 7,357,529 B2
(45) Date of Patent: Apr. 15, 2008

(54) VARIABLE INCIDENCE OBLIQUE ILLUMINATOR DEVICE

(76) Inventors: Albert Choate, 348 Honeoye Falls No. 6 Rd., Rush, NY (US) 14543; William R. Gilman, 78 Trotter Dr., Henrietta, NY (US) 14467

( * ) Notice: Subject to any disclaimer, the term of this patent is extended or adjusted under 35 U.S.C. 154(b) by 1222 days.

(21) Appl. No.: 10/082,842

(22) Filed: Feb. 21, 2002

(65) Prior Publication Data

US 2003/0156409 A1    Aug. 21, 2003

(51) Int. Cl.
*F21V 1/00*      (2006.01)
*F21V 11/00*    (2006.01)

(52) U.S. Cl. ............ 362/239; 362/237; 362/240; 362/289; 362/33; 359/387

(58) Field of Classification Search .......... 362/240, 362/237, 239, 250, 289, 285, 33; 359/382, 359/383, 385, 389, 387
See application file for complete search history.

(56) References Cited

U.S. PATENT DOCUMENTS 5,951,139 A * 9/1999 Smith et al. ............. 362/33
6,238,060 B1 * 5/2001 Bourn et al. ............. 362/216

* cited by examiner

*Primary Examiner*—Sandra O'Shea
*Assistant Examiner*—Ali Alavi
(74) *Attorney, Agent, or Firm*—Shlesinger, Fitzsimmons & Shlesinger

(57) ABSTRACT

The objective lens assembly of an optical inspection device is surrounded coaxially of its optical axis by an illuminator housing having therein a central opening surrounded by a circular array of reflective mirror surfaces or facets that are inclined at like angles to the optical axis, and which register with the light emitting of a like circular array of LEDs mounted in the housing in radially spaced, coaxial relation to the mirror facets. Mounted coaxially beneath the illuminator housing for vertical adjustment relative thereto is a generally disc-shaped Fresnel lens. The lens is movable by drive means optionally between an uppermost position adjacent the underside of the housing and a lowermost position adjacent the work that is to be inspected. When the lens in its uppermost position light beams from the LEDs are reflected by the mirror facets downwardly through an opening in the bottom of the illuminator housing in the form of an expanding cone of illumination and annularly onto the upper surface of the Fresnel lens. The Fresnel lens then refracts the cone of light and directs it toward the work that is to be inspected at an angle of incidence of 15° with respect to the optical axis. When the lens is shifted downwardly toward the workpiece, the angle of incidence of the refracted illumination increases to a maximum of 75°.

10 Claims, 3 Drawing Sheets

VARIABLE INCIDENCE OBLIQUE ILLUMINATOR DEVICE

BACKGROUND OF THE INVENTION

Figure 1:
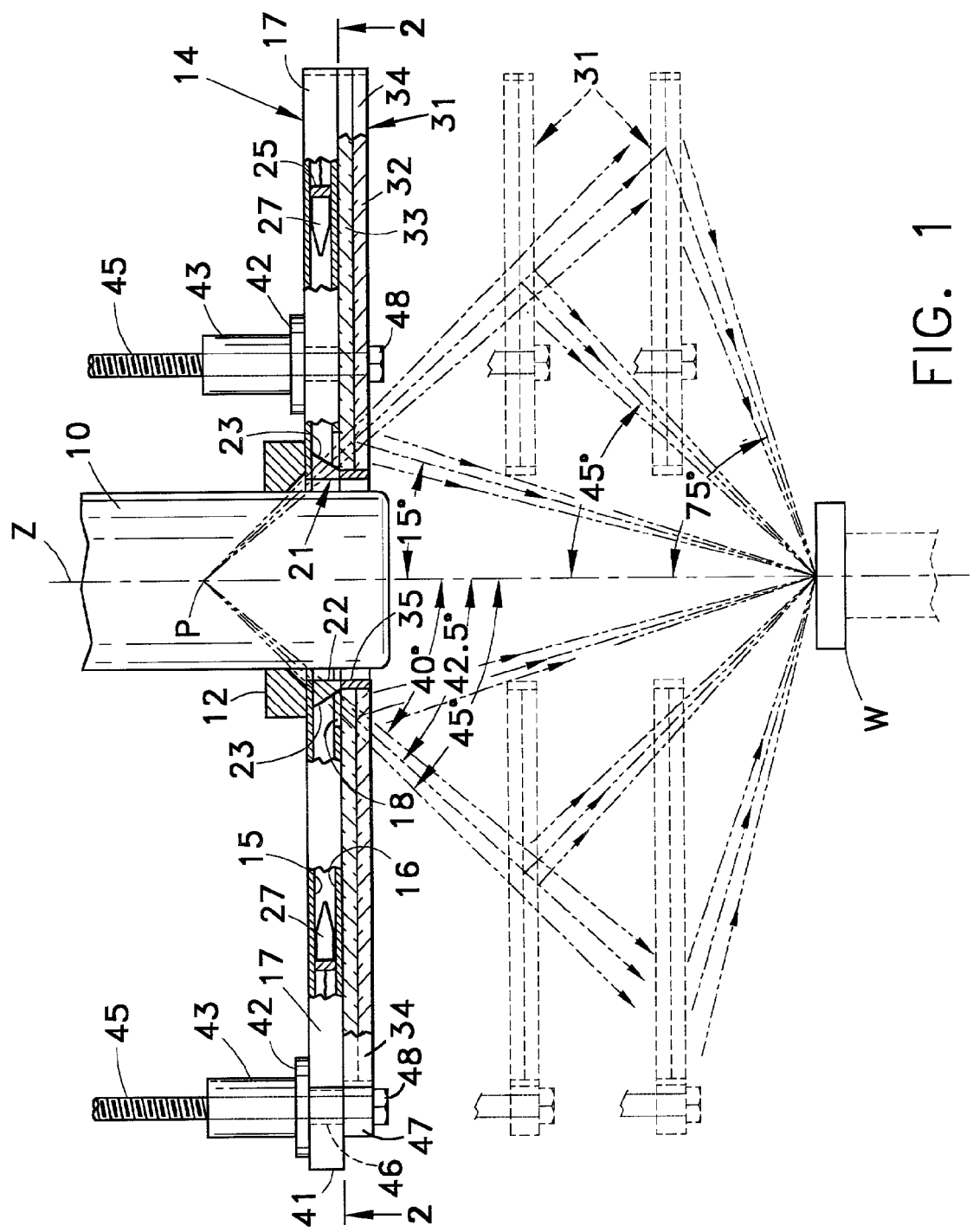

This invention relates to a variable incidence oblique illuminator device which is designed to be employed in optical inspection apparatus, and more particularly in apparatus of the type in which, relative to the associated optical axis, the angle of incidence of the light illuminating an object can be varied from 15° to 75°. Even more particularly this invention relates to a specially designed Fresnel lens moveable relative to the object that is being viewed to direct illumination at different angles of incidence onto the object.

Over the years a variety of apparatus have been developed for the purpose of illuminating an object which is to he inspected, for example items that are being inspected by countour projectors, optical comparitors, microscopes and other inspection systems. Typically an image of the illuminated object is then projected through a lens to an observer's eye, or more recently through video inspection apparatus. For best results, light or beams of light are directed obliquely downwardly onto an object that is being inspected better to illuminate edges or curved surfaces of an object. The oblique beams are directed at angles of incidence to the optical axis of the object that is being inspected. U S. Pat. No. 4,567,551, No. 5,897,195, No. 5,690,417 and No. 6,179,439, all of which are assigned to the same assignee as the present application, disclose a variety of different apparatus for projecting beams of light obliquely onto the surface of an object that is being inspected.

For example, U.S. Pat. No. 4,567,551, beaters from four different light sources are directed onto the reflective surfaces of four mirrors, which then reflect the light through a Fresnel lens onto the object that is to be inspected. In U.S. Pat. No. 5,897,195 a plurality of circular arrays of light emitting diodes (LEDs) surround a cylindrically shaped, Fresnel-like diffuser element which then directs the light beams from the LEDs at different angles of incidence to the optical axis of the apparatus, and onto the work that is being inspected. Variations of these multiple array LED illuminating systems are disclosed also in U.S. Pat. No. 5,690,417 and No. 6,179,439.

Although the above-noted apparatus disclose various ways of directing illumination at different angles of incidence onto an object that is being inspected, such apparatus also have the need for employing large arrays of light sources and associated Fresnel-like diffusers in order to direct onto a workpiece a large number of beams at different angles of incidence to the optical axis of the associated apparatus.

It is an object of this invention, therefore, to provide for such apparatus an improved illuminator device that employs only one circular array of light beams, and which array of beams can be directed optionally at different angles of incidence to the optical axis of the workpiece that is being inspected.

Still another object of this invention is to provide for apparatus of the type described an improved illuminator device having a circular array of light beams directed onto a Fresnel lens adjustable toward and away from art inspected object selectively to alter the angle of incidence of the light illuminating the object.

A further object of this invention is to provide for inspection apparatus an improved illuminator device of the type described which includes a Fresnel lens adjustable axially of the optical axis of the apparatus to focus light on an object and at selectively different angles of incidence to the optical axis.

Other objects of the invention will be apparent hereinafter from the specification and claims particularly when considered in conjunction with the accompanying drawings.

SUMMARY OF THE INVENTION

The cylindrical objective lens assembly of an optical inspection device is mounted above and focused upon the surface of a workpiece that is to be inspected. Adjacent its lower end the lens assembly projects coaxially into a central, circular opening formed in a generally disc-shaped illuminator housing, which is secured to and surrounds the lower end of the lens assembly coaxially thereof. Secured coaxially in the housing adjacent its central opening is a faceted annular mirror having formed on the inner side thereof which confronts upon the interior of the housing a circular array of reflective mirror surfaces or facets which are inclined at like angles to the optical axis, and to register with an annular opening formed in the bottom of the housing coaxially of the lens assembly. Secured in the housing coaxially of the optical axis is a circular array of LEDs equal in number to the mirror facets, and having the light emitting ends thereof disposed in radially spaced, confronting relation to the mirror facets.

Mounted coaxially beneath the illuminator housing for vertical adjustment relative thereto is a generally disc-shaped optical element which is similar in size to and in registry with the disc-shaped illuminator housing. The optical element comprises two disc-shaped plastic Fresnel lens elements having plane, flat outer surfaces, and grooved inner surfaces secured in confronting relation to each other. Optical element 31 is movable by drive means optionally between an uppermost position in which it is engaged with the underside of the illuminator housing, and a lowermost position in which it is spaced beneath the illuminator housing and closer to the work that is to be inspected. When the element is in its uppermost position light beams from the LEDs are reflected by the mirror facets downwardly at an angle of approximately 42½° through the annular opening in the bottom of the illuminator housing and annularly onto the upper surface of the optical element adjacent its radially inner end. The optical element then refracts the cone of light and directs it toward the work that is to be inspected, and at an angle of incidence of 15° with respect to the optical axis. As the optical element is shifted downwardly relative to the illuminator housing and toward the workpiece, the angle of incidence of the refracted illumination relative to the optical axis increases to a maximum of 75°.

THE DRAWINGS

Figure 2:
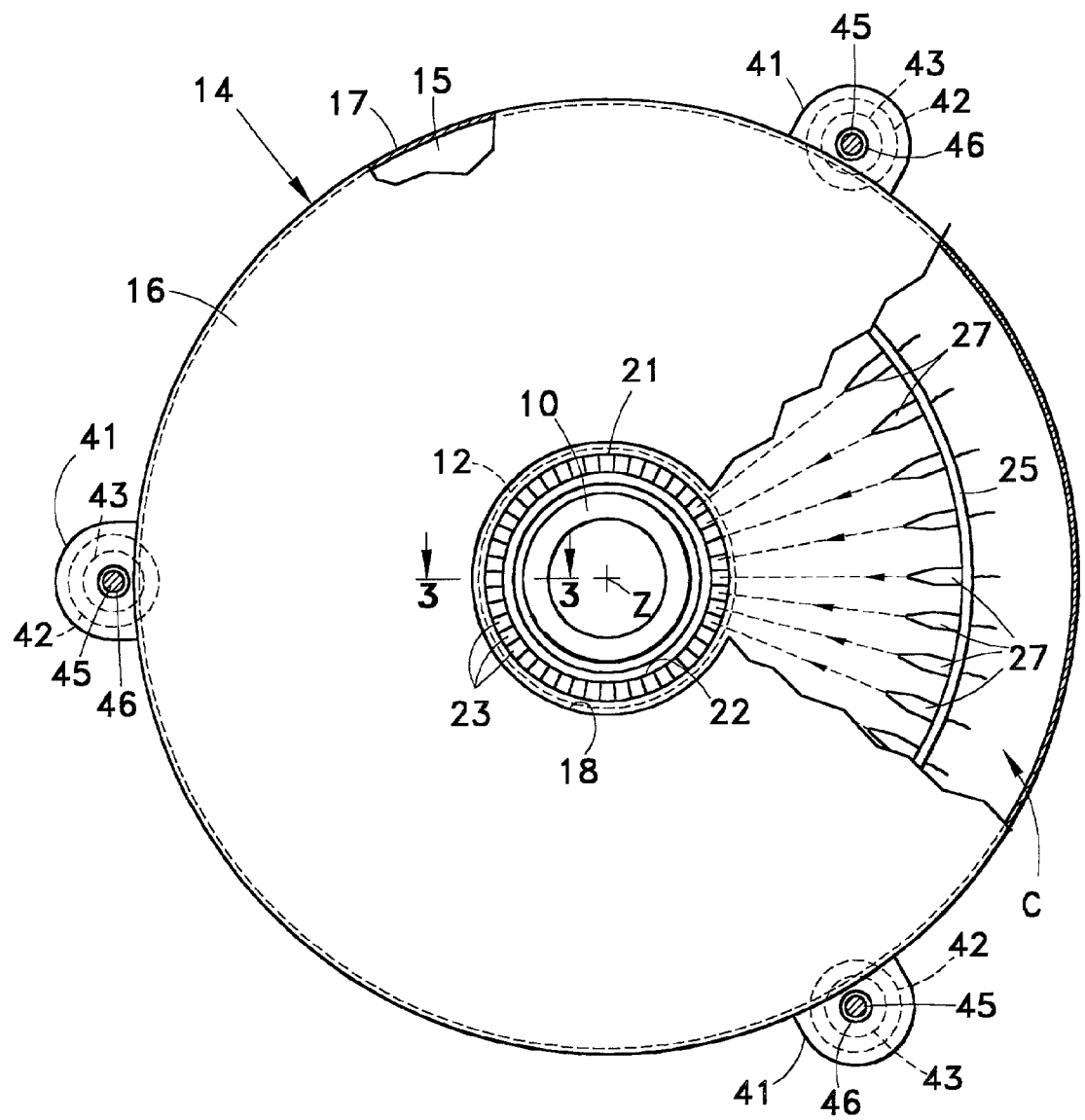
Figure 3:
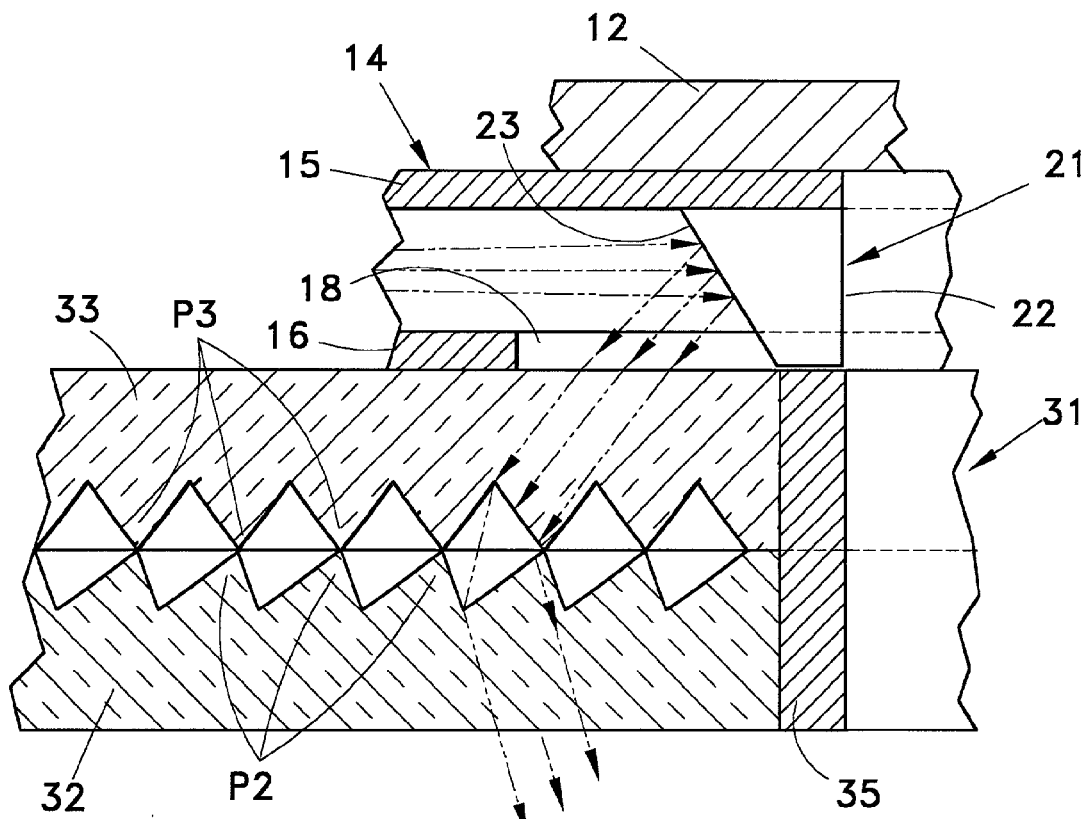
Figure 4:
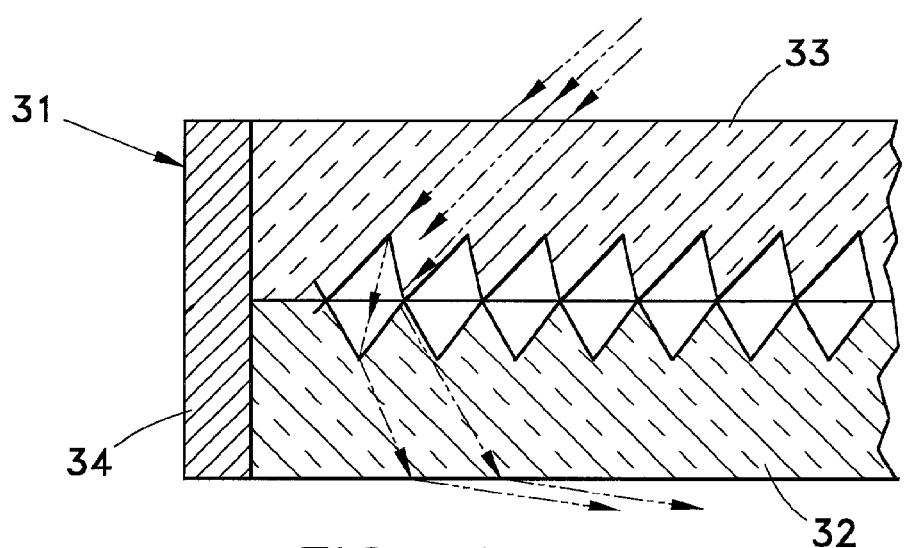

FIG. 1 is a fragmentary sectional view taken on a vertical plane through the axial centerline of an illuminator device made according to one embodiment of this invention, with the device's LED illuminator housing having portions thereof shown in full, and an associated Fresnel lens housing being shown in phantom by broken lines if two different positions which it can assume during operation of the device;

FIG. 2 is a sectional view taken generally along the line 2-2 in FIG. 1 looking in the direction of the arrows, and with a portion of the illuminator housing broken away for purposes of illustration;

FIG. 3 is an enlarged, fragmentary sectional view taken generally along line 3-3 in FIG. 2, and illustrating registering portions of the illuminator and Fresnel lens housings when the latter is in its uppermost position as shown in FIG. 1; and FIG. 4 is an enlarged, fragmentary sectional view taken through the Fresnel lens housing adjacent the outer peripheral surface thereof, when the Fresnel lens housing is in its lowermost position as illustrated in phantom in FIG. 1.

DETAILED DESCRIPTION OF THE PREFERRED EMBODIMENTS

Referring now to the drawings by numerals of reference, and first to FIGS. 1 and 2, 10 denotes the lower end of a cylindrical imaging objective lens assembly which is positioned above and focused upon the surface of a workpiece W (FIG. 1) which is to be inspected. Lens assembly 10 is disposed coaxially about the optical axis Z of an associated video camera (not illustrated), which is connected to the upper end of the lens assembly 10 in a conventional manner. Secured coaxially to and surrounding the lens assembly 10 adjacent its lower end is a rigid mounting collar 12. The lower end of assembly 10 extends slightly beyond the lower end of the collar 12, and coaxially through and in radially spaced relation to a circular opening formed in the center of a large, generally disc-shaped illuminator housing which is denoted generally by the numeral 14. Housing 14 comprises a pair of disc-.shaped upper and lower walls 15 and 16; respectively, having equal outer diameters and each having therethrough a central opening surrounding the lower end of lens assembly 10. The upper wall 15 has a portion of its outer surface secured in coplanar relation to the underside of the collar 12 coaxially thereof, and the lower wall 16 is maintained in spaced, parallel relation to the upper wall 15 by an annular outer wall 17, which is secured to and surrounds the walls 15 and 16 coaxially thereof, thereby to maintain them in axially spaced, coaxial relation to each outer. As shown more clearly in FIG. 1, the diameter of the central opening in the lower wall 16 of housing 14 is substantially larger than the diameter of the central opening in the upper wall 15, thereby forming in the bottom of housing 14, and centrally thereof, a circular opening 18 the purpose of which will be noted hereinafter.

Secured at its upper end coaxially to the inside surface of the upper housing wall 15 adjacent the central opening therein is a faceted annular mirror, which is denoted generally by the numeral 21 in FIGS. 1 through 3. Mirror 21 terminates at its lower end in housing 14 in registry with the opening 18 in the bottom wall 16, and has thereon coaxially of the optical axis Z an annular outer surface 22 disposed in radially spaced confronting relation to the lower end of the objective lens assembly 10. At the opposite or inner side thereof which confronts upon the interior of the illuminator housing 14, mirror 21 has formed thereon a circular array (forty-eight in the embodiment illustrated) of mirror surfaces or facets 23, the surfaces of which are inclined at like angles to the optical axis Z for a purpose noted hereinafter. Secured coaxially in the housing 14 between its upper and lower walls 15 and 16, and radially spaced from the outer wall 17 is an LED support ring 25. Secured at one end thereof to the inner peripheral surface of the ring 25 at angularly spaced points thereabout are the bases of a plurality (forty-eight in the embodiment illustrated) of light emitting diodes (LEDs) 27, the opposite, light emitting ends of which confront upon and register with the inclined mirror surfaces 23 of the faceted surfaces of mirror 21. The bases of the LEDs 27 are electrically connected in a conventional manner (not illustrated) with a power supply circuit which is mounted in the wiring channel C (FIG. 2) which is formed in housing 14 between its outer wall 17 and the LED supporting ring 25. Each of the LEDs 27, when illuminated, directs a beam of light, as shown for example in FIGS. 2 and 3, onto one of the facets 23, which beams are then directed downwardly through the opening 18 in the housing 14; as shown for example in FIG. 3, and at an angle to the optical axis Z which will be described in greater detail hereinafter.

Mounted coaxially beneath the housing 14 for vertical adjustment relative thereto is a generally disc-shaped optical element 31 having therethrough a central opening surrounding the lower end of the lens assembly 10 coaxially thereof. Element 31 comprises a pair of similar, disc-shaped plastic Fresnel lens elements 32 and 33 which have equal outside diameters, and central openings therethrough also of equal diameters. Elements 32 and 33 have plane, flat outer surfaces, and grooved or faceted surfaces secured in confronting, abutting, and coaxial relation to each other by a pair of rigid mounting rings 34 and 35, the former of which is secured to and surrounds the outer peripheral surfaces of the elements 32 and 33, and the other of which (ring 35) has its outer peripheral surface secured to the inner peripheral surfaces of the lens elements 32 and 33. As noted above, the elements 32 and 33 have confronting faceted surfaces the details of which will be described in further detail hereinafter.

For use in shifting the optical element 31 vertically relative to the bottom of the illuminator housing 14 three nearly semicircular mounting plates 41 (FIG. 2) are secured to and project from the outer peripheral surface from the housing wall 17 at approximately 120° intervals thereabout. Secured to the upper surface of each plate 41 is the mounting flange 42 of a conventional stepper motor 43, which may be of the type known as the AIRPAX stepper motor from Cheshier, Conn. Each such motor operates an externally threaded shaft 45, which is mounted in an axial bore in the associated motor housing for movement by the motor selectively in opposite directions. As shown more clearly in FIGS. 1 and 2, each externally threaded shaft 45 projects out of the lower end of its associated motor housing 43 and coaxially through and in radially spaced relation to the annular wall of a central opening 46 which is located in the associated mounting plate 41. Secured to the outer peripheral surface of the optical element ring 34 beneath and in registry with the plates 41 are three small brackets 47. The lower end of each shaft 45 threads through a central opening in the registering bracket 47 and into a locknut 48 engaged with the underside of the bracket. In this manner the optical element 31 is secured to the lower ends of shafts 45 for vertical movement thereby between an elevated position in which it is engaged with the underside of housing 17, as shown by full lines in FIG. 1, and any of a variety of adjusted positions in which it is axially spaced beneath housing 17, two of which positions are shown for example by broken lines in FIG. 1.

Referring now to FIGS. 3 and 4, wherein the confronting, grooved surfaces of the Fresnel elements 32 and 33 are illustrated in greater detail, it will be noted that each of the confronting surfaces has formed coaxially therein a series of radially spaced circular grooves which form in each surface a series of radially spaced circular facets facing each other, and in such manner that the opposing peaks (P2 of element 32 and P3 of element 33) are accurately aligned to confront upon each other thereby to maximize illumination transmission. This construction incidentally, is most commonly employed in overhead projector systems. Each of the forty-eight LEDs 27 emits a beam of light which has a slight angular spread (as shown in FIG. 3) so that when a LED beam strikes one of the faceted mirror surfaces 23, it is directed by the associated facet 23 downwardly through the opening 18 at an angle of 42½°. As shown in FIG. 1 this results in a downward expanding ring of illumination in the form of a cone having, for example as shown in FIG. 1 an inside angle of 40°, a central angle of 4½°, and an outside angle of 45°, which cone appears to emanate from a common point P on the optical axis Z. The resulting cone of light formed by the beams reflected from the faceted mirror surfaces 23 project through the opening 18 and illuminate an annular or ring-shaped region of the Fresnel lens formed by sections 32 and 33 thereof. As shown more clearly in FIGS. 1 and 3, this ring-shaped region of light is redirected by the facets of the Fresnel lens and focused at an angle of 15° to the optical axis Z onto the object plane or surface of the workpiece W that is to be inspected.

As the optical element 31 (the Fresnel lens) is moved downwardly toward the object plane—i.e., toward the workpiece W—the cone of light engaging the Fresnel lens in its adjusted position, still intersects the lens at the same angle as noted above (from 40° to 45°) but of course at progressively larger radii from the optical axis. While for different positions of the optical element 31 (the Fresnel lens) relative to housing 17 the central angle of the light entering the lens from the illuminator housing 17 will always be 42½°, the outgoing angle of the refracted light—the light from the Fresnel lens which is focused thereby on the object plane—increases progressively as element 31 approaches the object plane (the work W). It is this particular geometrical relationship which defines the facet deflection requirements for the different positions of the Fresnel lens. In the case of the elements 32 and 33 the angles of the facets in their confronting surfaces vary from the radially innermost to the radially outermost thereof in order to achieve the refraction range of 15° to 75°.

In view of the foregoing, the Fresnel lens is specifically designed for each of its positions relative to the housing 17, to focus the incoming cone of light from the illuminator housing 17 onto the object or work W that is being inspected. With the present invention it is possible to have light emitted from the Fresnel lens at an angle of incidence to the optical axis Z at anywhere from 15° to 75° simply by adjusting the position of the optical element 31 vertically relative to the illuminator housing 14.

From the foregoing it will be apparent that the use of the adjustable Fresnel lens provides a reliable and effective means for focusing a cone of light onto an object plane (workpiece surface) at angles of incidence relative to the associated optical axis in the range of 15° to 75°. While in the illustrated embodiment the light emitted from the mirror facets 23 is directed directly onto the associated Fresnel lens, it would be within the scope of this invention also to employ, if desired, a slightly diffusing surface on the top side of the lens element 33 to expand the region projected onto the work W, or somewhat to homogenize the illumination. Each of the LEDs employed herein embody a small emitting source embedded within a collimating lens, so that collimated beams of light are directed radially and in a common plane onto the registering mirror facets 23. However, it is to be understood that a plurality of small incandescent sources or fiber optic conduits or lasers with collimating lenses could serve the same purpose. Also, if desired, colored filtering or strobing may be employed, as well as, if desired, discrete sources that control which light sources around the incident cone may be selectively activated.

While this invention has been illustrated and described in connection with only certain embodiment thereof, it will be apparent that this application is intended to cover any such modifications as may fall within the scope of one skilled in the art, or the appended claims.

The invention claimed is:

1. In combination with an objective lens assembly disposed coaxially of the optical axis of an inspection device for projecting thereto an image of the illuminated surface of a workpiece spaced beneath and in registry with said assembly, a variable incidence oblique illuminator, comprising
   a housing secured to and surrounding said assembly,
   illuminating means in said housing for directing an expanding cone of illumination toward said workpiece coaxially of said optical axis,
   a focusing element positioned between said housing and said workpiece in the path of said cone coaxially thereof, and operative to redirect and focus said cone of illumination onto the surface of said workpiece at a predetermined angle of incidence relative to said optical axis, and
   means mounting said focusing element for limited movement longitudinally of said axis between said housing and said workpiece, said element being operative to decrease said angle of incidence upon approaching said housing, and to increase said angle of incidence upon approaching said workpiece.

2. The combination as defined in claim 1, wherein said mounting means includes means for moving said element into different positions of rest between a first limit position in which said angle of incidence amounts to 15°, to a second limit position in which said angle of incidence amounts to 75°.

3. The combination as defined in claim 2, wherein said focusing element is a Fresnel lens.

4. The combination as defined in claim 1, wherein said illuminating means comprises
   an annular array of narrow-beam light sources mounted in said housing coaxially of said axis and operative to direct an array of light beams radially toward said axis, and
   a like annular array of mirrors mounted in said housing coaxially and radially inwardly of said light sources to register with the beams therefrom,
   said mirrors being inclined to said axis and being operative to direct said light beams as said expanding cone of illumination onto said focusing element at a predetermined angle of incidence relative to said optical axis.

5. The combination as defined in claim 4, wherein said light sources comprise a plurality of collimated light emitting diodes.

6. The combination as defined in claim 3, wherein said Fresnel lens comprises
   a pair of similar, disc-shaped Fresnel lens elements having therethrough registering central openings disposed coaxially of said optical axis,
   each of said lens elements having a plurality of radially spaced circular, light refracting facets formed on one surface thereof, and
   means securing said elements together with the faceted surfaces thereof disposed in confronting, coaxial relation to each other.

7. The combination as defined in claim 2, wherein said illuminating means is operative for each of said different positions of said focusing element to direct said expanding cone of illumination onto said element at the same angle of incidence relative to said optical axis.

8. The combination as defined in claim 7, wherein said same angle of incidence is 42½°.

9. The combination as defined in claim 1, wherein
said focusing element comprises a disc-shaped Fresnel lens having therein a central opening registering coaxially with said lens assembly, and being movable between a first limit position adjacent said housing, and a second limit position adjacent said workpiece, and
said illuminating means being operative to direct said cone of illumination onto said Fresnel lens at a fixed angle of incidence relative to said optical axis for all different positions of said lens.

10. The combination as defined in claim 9, wherein said illuminating means comprises,
a circular array of collimated light emitting diodes disposed coaxially in said housing and operable to direct light beams radially towards said optical axis, and
a like array of mirrors interposed in the path of said beams between said diodes and said axis and operative to direct said beams in the form of said expanding cone of illumination onto said Fresnel lens at an angle of incidents relative to said optical axis which is the same for all said positions of said lens.

* * * * *

UNITED STATES PATENT AND TRADEMARK OFFICE
CERTIFICATE OF CORRECTION

| | | |
|---|---|---|
| PATENT NO. | : 7,357,529 B2 | Page 1 of 1 |
| APPLICATION NO. | : 10/082842 | |
| DATED | : April 15, 2008 | |
| INVENTOR(S) | : Albert G. Choate and William R. Gillman | |

It is certified that error appears in the above-identified patent and that said Letters Patent is hereby corrected as shown below:

On the Title Page, Item (73) the assignee is not named. The assignee should be indicated as follows:

Assignee: Optical Gaging Products, Inc., Rochester NY (US)

Signed and Sealed this

Eleventh Day of August, 2009

David J. Kappos
*Director of the United States Patent and Trademark Office*